United States Patent [19]

Cartilier et al.

[11] Patent Number: 5,989,589
[45] Date of Patent: Nov. 23, 1999

[54] CROSS-LINKED CELLULOSE AS A TABLET EXCIPIENT

[76] Inventors: Louis Cartilier, 242 Hollis Road, Beaconsfield, Quebec, Canada, H9W 2M7; Chafic Chebli, 3070 Chemin Lake, Dollard-des-Ormeaux, Quebec, Canada, H9G 2V5

[21] Appl. No.: 08/956,117

[22] Filed: Oct. 24, 1997

[51] Int. Cl.⁶ .................................................... A61K 9/22
[52] U.S. Cl. ..................... 424/465; 424/464; 424/488; 424/489; 424/494; 514/960; 514/961
[58] Field of Search ................................. 424/464, 465, 424/488, 489, 494; 514/960, 961

[56] References Cited

U.S. PATENT DOCUMENTS

| | | |
|---|---|---|
| 3,453,368 | 7/1969 | Magid . |
| 3,622,677 | 11/1971 | Short et al. . |
| 3,725,556 | 4/1973 | Hanssen et al. . |
| 4,369,308 | 1/1983 | Trubiano . |
| 4,933,185 | 6/1990 | Wheatley et al. . |
| 5,456,921 | 10/1995 | Mateescu et al. . |
| 5,603,956 | 2/1997 | Mateescu et al. . |
| 5,616,343 | 4/1997 | Cartlilier et al. . |
| 5,776,492 | 7/1998 | Betzing et al. . |

FOREIGN PATENT DOCUMENTS

| | | |
|---|---|---|
| 94/02121 | 2/1994 | WIPO . |
| 94/21236 | 9/1994 | WIPO . |
| 98/03064 | 1/1998 | WIPO . |

*Primary Examiner*—Thurman K. Page
*Assistant Examiner*—Brian K. Seidleck
*Attorney, Agent, or Firm*—ROBIC

[57] ABSTRACT

Cross-linked cellulose is an excellent binder disintegrant that can be used in the preparation of pharmaceutical tablets. The tablets that are so prepared are made of a compressed mixture of a powder of a pharmaceutically active ingredient with a powder of a pharmaceutical excipient including a pharmaceutically acceptable form of cross-linked cellulose in an amount up to 35% by weight with respect to the total weight of the tablet. The cross-linked cellulose is prepared by cross-linking microcrystalline or fibrous cellulose with a cross-linking agent such as epichlorhydrin in a relative amount of 2 to 50 g of cross-linking agent per 100 g of cellulose. Tests have proved that cross-linked cellulose is very easy to synthetise and has excellent binding/disintegrating properties that are function of the cross-linking degree. At low cross-linking degree, cross-linked cellulose is more a binder than a disintegrant whereas at high cross-linking degree, it is more a disintegrant than a binder.

14 Claims, 7 Drawing Sheets

CROSS-LINKED CELLULOSE AS A TABLET EXCIPIENT

FIELD OF THE INVENTION

The present invention relates to the use of cross-linked cellulose as a binder and/or disintegrant in a pharmaceutical tablet prepared by direct compression.

BRIEF DESCRIPTION OF THE PRIOR ART

In the pharmaceutical industry, tablets appear to be the most advantageous form for the administration of a drug. Packaging and handling are normal operations onto which pharmaceutical products are submitted, which makes tablets the preferred choice. Additionally, tablets are frequently employed in non-pharmaceutical fields such as fish foods, plant growth regulators, pesticides, herbicides and the like.

The simplest and most economical procedure for the manufacturing of tablets is the direct compression of all the ingredients distributed homogeneously. The powder compression in a tablet puncher follows directly the dry blending of one or more active ingredients with at least one pharmaceutical excipient selected amongst diluents, fillers, binders, disintegrants, lubricants and the like.

Diluents or fillers are added to increase bulk to the formulation, and lubricants, to reduce friction during the tableting process.

Binders are used for tableting some pharmaceutical ingredients. They provide the cohesiveness necessary for bonding together the ingredient granules under compression. Binders (also called hereinafter "binding agents") also increase the strength of the compressed tablet and decrease its friability, leading to an improvement in the tablet appearance and mechanical characteristics. An appropriate binding agent shows flowing properties, can be blended easily and is inert and non-toxic. Conventional binders currently in use include: microcrystalline cellulose (Avicel PH101® and Avicel PH102®), polyvinylpyrrolidone (Kollidon™, Plasdone™), cornstarch, modified starches, gums, and the like. These binders are usually employed in direct compression at a concentration level of about 20% by weight.

In practice, the quantity of binder used in a formulation must be carefully regulated, since the tablet must disintegrate after administration to liberate the drug.

For this purpose, disintegrants are usually added to cause the compressed tablet to break immediately apart when placed in an aqueous medium. Typical disintegrants are gelatinised starches (Sta Rx™) or modified starches, e.g. sodium starch glycolate (Primojel™). Some of these disintegrants are called superdisintegrants because of their high efficiency, even at low concentration, and because of their high swelling capacity in the presence of water.

It is also known that some materials, such as microcrystalline cellulose (Avicel PH101® and Avicel PH102®) present binding and disintegrating characteristics and therefore are useful both as a binder and a disintegrant.

Despite the existence of many binders and disintegrants, pharmaceutical researchers continue their efforts to develop improved materials capable of being employed as a binder and/or disintegrant in the preparation of tablets obtained by direct compression. Particularly, there is still a need for a versatile binder/disintegrant, which should be efficient regardless of the solubility of the diluent or the active ingredient.

On the other hand, cross-linked cellulose is well known in the literature. It is very important in textiles. The chemical nature of the cross-links may vary from ether to ester. Among the oldest cross-linking agents that have been used, one can mention formaldehyde, which imparts improved wet strength to cellulose [X. Eschalier, *J. Chem. Soc. Ind. London* 26, 821 (1907)], and N-hydroxymethyl compounds that improve the dimensional stability and increase resistance and durable press-properties of textiles. Other compounds that have been investigated as cellulose cross-linking agents and that function in this application by forming ether bonds include divinyl sulfone [see U.S. Pat. No. 2,524,399 to D. L. Schoene and V. S. Chambers], tris(azyridinyl) phosphine oxide [see W. A. Reeves et al, *Text. Res. J.* 27,260 (1957)] and epichlorohydrin, i.e. via an epoxide intermediate [J. B. McKelvey et al., *J. Appl. Polym. Sci.* 7, 1371 (1963)].

As aforesaid, cross-linked cellulose has been used so far in the textile industry only. As already mentioned hereinabove, some other cellulose derivatives and other cross-linked polymers have already been proposed as binders and/or disintegrants in the pharmaceutical industry. However, to the Applicant's knowledge, noone has suggested so far to use cross-linked cellulose in this industry.

By way of example, U.S. Pat. Nos. 2,978,446; 3,141,875 and 3,023,104 to Battista disclose a microcrystalline form of cellulose where crystalline cellulosic aggregates are prepared in an acid medium. This product is well known as a binder/disintegrant in the pharmaceutical industry and different embodiments of it are presently sold under the trademark of Avicel PH101® and Avicel PH102®. It is worth mentioning however that no chemical cross-linking is involved in the preparation of these products.

U.S. Pat. No. 5,272,191 to Herber et al discloses a water insoluble cellulose material what is sold under the trademark Ac-Di-Sol™ (which is the acronym of Accelerated Dissolution), to promote fast disintegration of pharmaceutical dosage forms. This product is obtained by internally cross-linking sodium carboxymethylcellulose. The cross-linking is achieved thermally without the use of any chemical additive (viz. cross-linking agent) to create a bridge between the macromolecular chains of cellulose. Ac-Di-Sol™ is known to quickly absorb high amounts of water by swelling, thereby leading to the disintegration of the tablet. Thus, the structure and process of preparation of this product are very different from those of cross-linked cellulose.

International laid-open patent application WO 94/21236 to Cartilier et al discloses powders of cross-linked amylose having a specific cross-linking degree for use as a binder/disintegrant. The tablets are prepared by direct compression. Cross-linked amylose tablets with a low cross-linking degree swell in aqueous media, allowing a hydrophilic matrix type controlled release of the drug throughout a gel layer [see also U.S. Pat. No. 5,456,921 and international laid-open patent application No. WO 94/02121 to Mateescu et al.]. Powders of cross-linked amylose with a high cross-linking degree allow tablets to disintegrate quickly by their high capacity of water absorption and their swelling power. Once again, it can be emphasized that amylose and cellulose have different chemical structures leading to different macromolecular aspects and thus to very different physico-chemical properties.

SUMMARY OF THE INVENTION

Surprisingly, it has now been discovered that cross-linked cellulose is an excellent binder/disintegrant and can therefore be used for the preparation of tablets. More specifically, it has been discovered that the behaviour and mechanism of action of cross-linked cellulose as a disintegrant are substantially different from those of "similar" products, like the one sold under the trademark Ac-Di-Sol™, inasmuch as cross-linked cellulose does not swell in the presence of water whatever is its degree of cross-linking thereby leading to a different efficiency, as it will be demonstrated hereinafter.

Thus, the present invention is directed to the use of cross-linked cellulose as a binder/disintegrant in the formulation of a pharmaceutical tablet prepared by direct compression.

The pharmaceutical tablet that is so prepared consists of a compressed dry mixture of a powder of at least one pharmaceutically active ingredient with a powder of at least one pharmaceutical excipient including a binder/disintegrant present in an amount equal to or lower then 35% by weight with respect the total weight of the tablet.

In accordance with the invention, the binder/disintegrant used in this tablet is a pharmaceutically acceptable non-swelling cross-linked cellulose having a cross-linking degree ranging from 2 to 50. This cross-linked cellulose is prepared by cross-linking cellulose selected from the group consisting of fibrous cellulose and microcrystalline cellulose, with a cross-linking agent in a relative amount of 2 to 50 g of cross-linking agent per 100 g of cellulose.

The above mentioned relative amount is based on the use of epichlorhydrin as cross-linking agent. However, it can also be adapted to any other cross-linking agent, like those named hereinafter.

Tests carried out on tablets having the above formulation have proved that cross-linked cellulose (CLC) polymers are interesting excipients for the preparation of tablets. CLC polymers can be differentiated from the other excipients by the fact that they are very easy to synthesise and their binding/disintegrating properties are function of the cross-linking degree. Thus, CLC polymers may respond to any formulator needs, when knowing that at low cross-linking degrees, CLC polymer is more a binder than a disintegrant, whereas at high cross-linking degree, it is more a disintegrant than a binder.

The invention and its advantages will be better understood upon reading of the following non-restrictive detailed description and examples made with reference to the accompanying drawings.

In these following description and examples, the various cross-linked cellulose polymers according to the invention that were prepared and tested, have been identified by the symbol:

CLC-tn wherein

CLC stands for "cross-linked cellulose";

t is C or F, C being the abbreviation of the word "microcrystalline" and F of the word "fibrous", both of the abbreviations being indicative of the type of cellulose that is used; and n is the degree of cross-linking expressed as the ratio of g. of cross-linking agent (essentially epichlorhydrin) to 100 g of cellulose.

DETAILED DESCRIPTION OF THE INVENTION

As aforesaid, the present invention lies in the use of cross-linked cellulose as a binder/disintegrant in a pharmaceutical tablet consisting of a compressed drug mixture of a powder of at least one pharmaceutically active ingredient with a powder of at least one pharmaceutical excipient including, of course, the above mentioned binder/disintegrant.

The cross-linked cellulose that is used must be a pharmaceutically acceptable cross-linked cellulose. It has a cross-linking degree ranging from 2 to 50, preferably from 3 to 40, and it is prepared by cross-linking cellulose with a cross-linking agent in a relative amount of 2 to 50 g of cross-linking agent per 100 g of cellulose.

The cross-linked amylose acting as a binder/disintegrant is present in the tablet in amount equal to or lower than 35% by weight with respect to the total weight of the tablet. Preferably, such amount ranges from 2 to 20% and, more preferably, from 10 to 20% by weight.

The cellulose used to prepare the cross-linked cellulose can be fibrous cellulose or microcrystalline cellulose.

The cross-liking agent used to cross-link the cellulose can be epichlorhydrin, sodium trimetaphosphate (STMP), adipic-acetic anhydride, phosphorus oxychloride, formaldehyde or a diepoxide, such as vinylcyclohexene dioxide or butadiene dioxide. Preferably, use is made of epihclorhydrin or STMP.

The tablets can be prepared by dry mixing the active ingredient with the excipient and then compressing the so obtained mixture in a conventional tablet puncher. In addition to the cross-linked cellulose, the excipient may also include one or more other additives selected amongst all the conventional tablet additives used in the pharmaceutical industry. Such additives include fillers, diluents, lubricants and the like.

To better illustrate the present invention, tablets containing cross-linked cellulose (CLC), magnesium stereate as a lubricant and Encompress®, Spray-dried lactose® or Lactose 100 mesh® as a diluent were prepared. The granule swelling power, the rate and the amount of water uptake of the tablets were determined. The influence of different diluents was evaluated by measuring the disintegration time and the crushing strength of the tablets. The effect of CLC concentration on the physical properties such as crushing strength and disintegration time of direct compressed tablets was also studied.

The results that were obtained, show that cross-linked cellulose has excellent binding and/or disintegrating properties. The binding and disintegrating properties of the CLC polymers that were prepared and tested are function of the cross-linking degree (n). At low cross-linking degrees ($n \leq 20$), the CLC polymers are more binders than disintegrants. However, at high cross-linking degrees ($n \geq 30$), the CLC polymers are more disintegrants than binders. Consequently, CLC polymers having a "medium" cross-linking degree (20<n<30), like for example, CLC-C25, are very efficient as binding/disintegrating agents regardless of the diluent) or active ingredient) solubility.

As a matter of fact, the disintegrant properties of the CLC polymers are comparable or even superior in some instances to those of cross-linked carboxymethylcellulose (Ac-Di-Sol™), a superdisintegrant known for its high efficiency.

As for the binding properties of the CLC polymers, they are clearly superior both those of Avicel PH101® and Avicel PH102®, two binding/disintegrating agents widely used in tablet manufacture. It should be noted that the unexpected and highly effective binding properties of cross-linked cellulose, regardless of the diluent solubility, have not been observed with cross-linked carboxymethylcellulose.

Cross-linked cellulose

Cellulose is a polymer of D-glucose in which the individual units are linked by β-glucosidic bonds form the anomeric carbon of one unit to the CA4 hydroxyl of the next unit. It is a linear polysaccharide, the isolated form containing an average of 3000 units per chain, corresponding to an average molecular weight of about 500,000. It is a natural polysaccharide, where hydroxyl groups of each glucose have different reactivities. The C-6 OH group ($OH^1$) is the most reactive (primary carbon), the C-2 OH group is less reactive ($OH^2$) and the C-3 OH group ($OH^3$) is the weakest for the "bent" conformation with reasonable distance which allows the formation of a hydrogen bond between C-3 OH and the neighbouring oxygen molecule.

To prepare the cross-linked cellulose used in the tests, cellulose was swollen in an alkaline medium such as sodium hydroxide on ice. After complete homogenization, an appropriate amount of cross-linking agent was added and homogenization continued for 15 minutes. The milky solution was then heated gradually to 60–65° C. The obtained gel was then neutralised with distilled water and washed acetone/ water and finally dried with acetone. The resulting solid gel was exposed overnight to air.

Preparation of tablets

Different lots of tablets were prepared with different diluents, as described in the following Table 1, using a hydraulic press (C-30 Research & Industrial Instruments Company, London, U.K.). The tablets that were so prepared, weighted 500 mg each and included in their composition a diluent (Encompress®, Lactose 100 mesh® or Spray-dried lactose®), various concentrations of binder/disintegrant (CLC, Avicel PH101® or Avicel PH102®), a superdisintegrating agent (Ac-Di-Sol™) and 0.5% of magnesium stereate as a lubricant.

TABLE 1

| | Tablet composition | | | |
|---|---|---|---|---|
| Filler | Disintegrant (%) | Binder/Disintegrant (%) | Lubricant (%) |
| Emcompress ® (add to 100%) | Ac-Di-Sol ® (2, 3, 5, 10, 15 & 20) | — | Mg stearate (0.5) |
| | — | CLC-C25 (2, 3, 5, 10, 15 & 20) | Mg stearate (0.5) |
| | — | Avicel PH101 ® (2, 3, 5, 10, 15 & 20) | Mg stearate (0.5) |
| | — | Avicel PH102 ® (2, 3, 5, 10, 15 & 20) | Mg stearate (0.5) |
| Lactose 100 mesh ® (add to 100%) | Ac-Di-Sol ® (2, 3, 5, 10, 15, & 20) | — | Mg stearate (0.5) |
| | — | CLC-C25 (2, 3, 5, 10, 15 & 20) | Mg stearate (0.5) |
| | — | Avicel PH101 ® (2, 3, 5, 10, 15 & 20) | Mg stearate (0.5) |
| | — | Avicel PH102 ® (2, 3, 5, 10, 15 & 20) | Mg stearate (0.5) |
| Spray-dried lactose ® (add to 100%) | Ac-Di-Sol ® (2, 3, 5, 10, 15, & 20) | — | Mg stearate (0.5) |
| | — | CLC-C25 (2, 3, 5, 10, 15 & 20) | Mg stearate (0.5) |
| | — | Avicel PH101 ® (2, 3, 5, 10, 15 & 20) | Mg stearate (0.5) |
| | — | Avicel PH102 ® (2, 3, 5, 10, 15 & 20) | Mg stearate (0.5) |

Distintegration of tablets

Disintegrating time was measured in distilled water at 37±1° C., pH 6.5, according to the method described by the U.S. Pharmacopoeia USP XXIII -<2040>*Disintegration and Dissolution of Nutritional Supplements,* using a tablet disintegration tester apparatus (Vanderkamp Tablet Disintegration Tester, Van-Kel Industries Inc., New Jersey, USA). The tablets were considered completely disintegrated when all particles passed through the wire mesh. Tablets with a surface erosion disintegration pattern retained their shape and only reduced their size with time. At least three measurements were taken for each tablet formulation. Mean values and standard deviations were calculated.

Tablets hardness

Crushing strength of the tablets was estimated on the Amtrex Schleuniger-4M tablet hardness tester (Vector Corporation, Iowa, USA). At least three tablets from each formulation were sued in each determination and the mean values expressed in kg force.

Water penetration into tablets

The method adopted to measure the rate of water penetration into tablets was similar to that described by several investigators [Pourkavoos N. et al., *Pharm. Res.* 10(9), 13363–1371 (1993); Sheen P. et al., *Drug Dev. Ind. Pharm.*, 15(3), 401–414 (1989) and Van Kamp H. V. et al, *Pharm. Acta Helv.* 61(1), 22–29 (1986)]. The apparatus consisted of a fritted glass disk filter (Pyrex, USA No. 36060, 15 ml, ASTM 40–60) connected to a 2-mL pipette (0.01 -mL divisions) via tygon tubing. The filter and the pipette were in a vertical position. The assembly was filled with distilled water and adjusted to zero reading on the pipette. The tablet was placed in direct contact with the moist fritted glass disk, so water could draw into the tablet though it. Water uptake was recorded as the change in water level in the pipette versus time at room temperature. Three measurements were taken for each excipient. Tablets weighting 500 mg each, compressed on a hydraulic press at 2 tons/cm$^2$ compression force, were studied. They contained 100% of the excipient studied.

Figure 1:
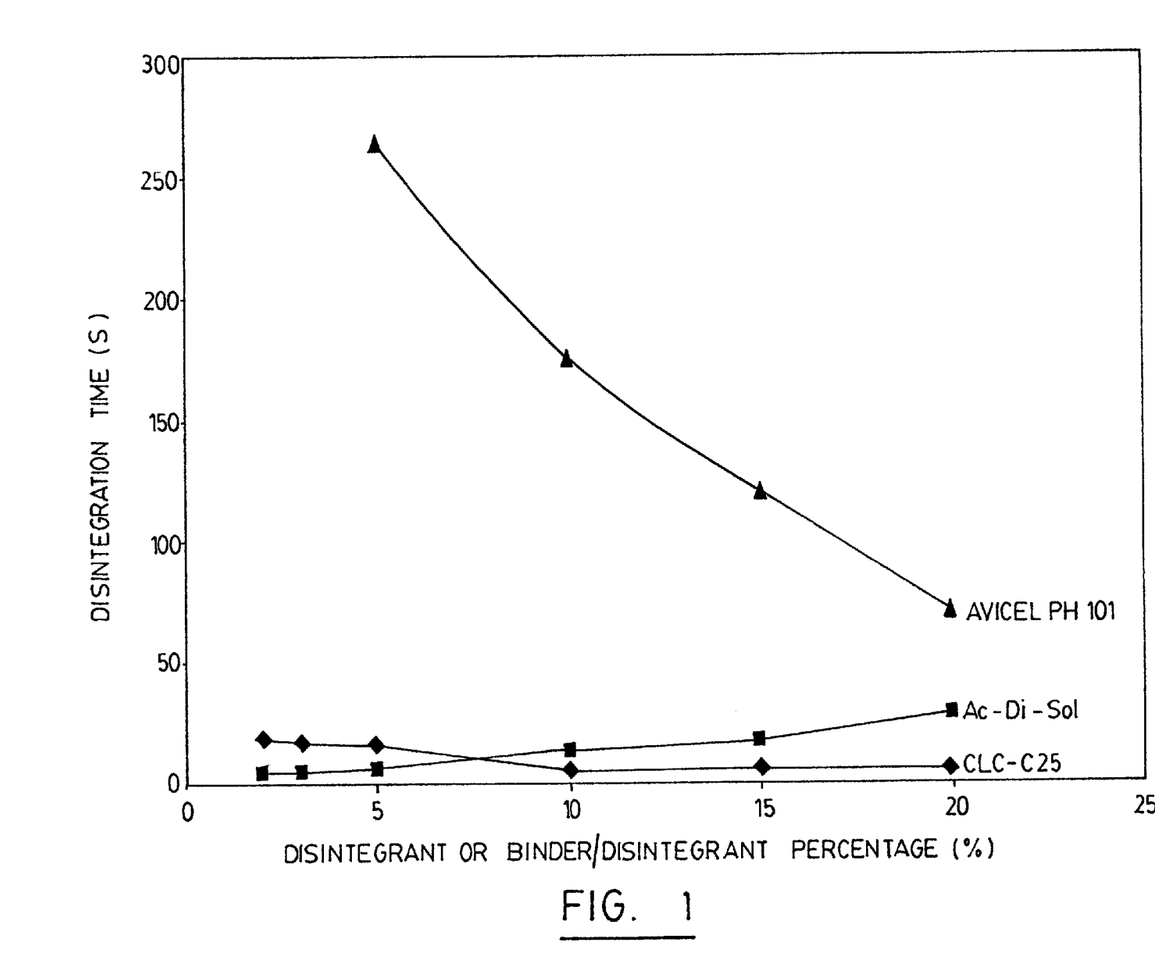
FIG. 1 is a curve illustrating disintegration tests for CLC-C25 tablets containing Encompress® as a filler.
Figure 2:
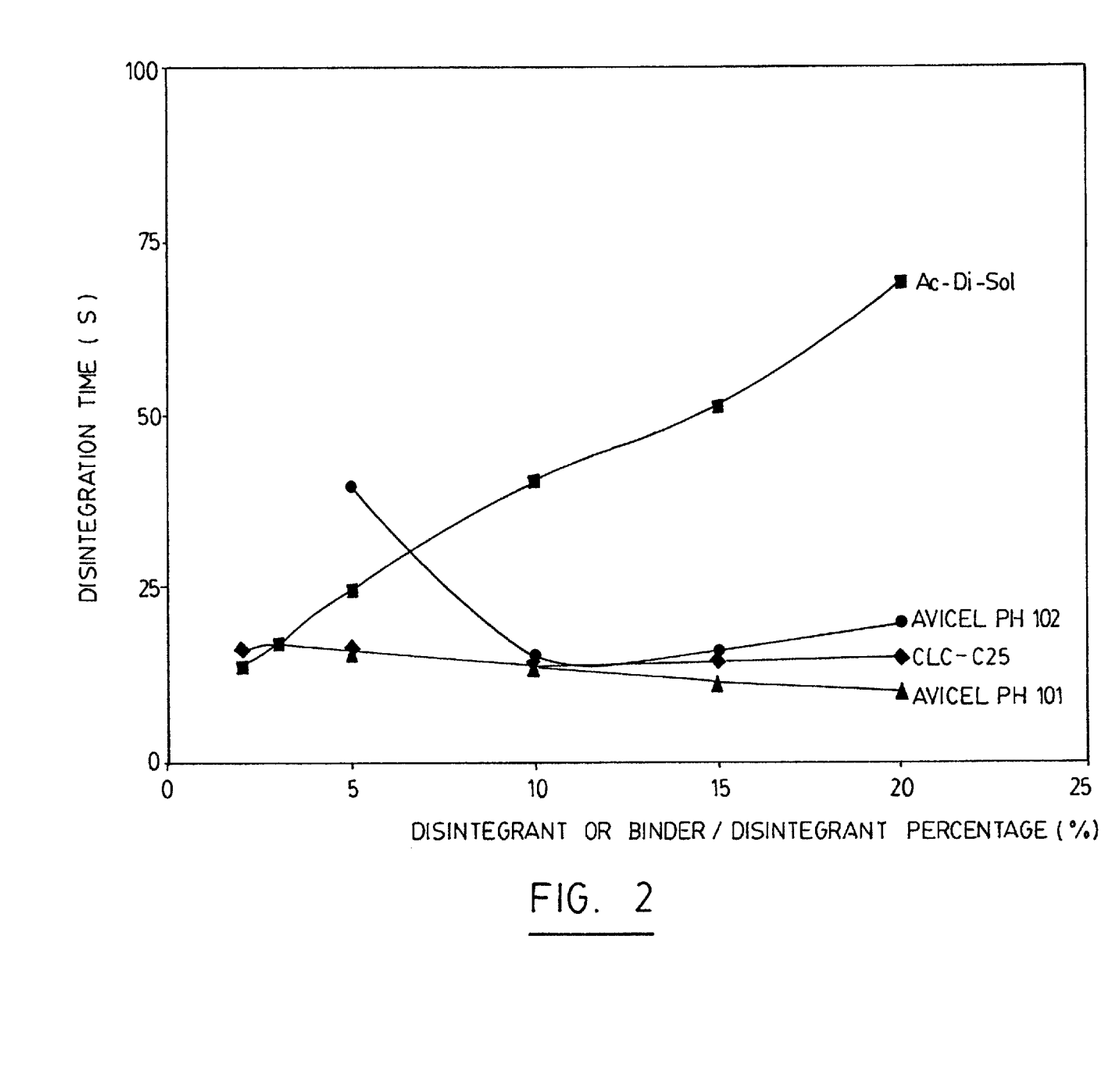
FIG. 2 is a curve illustrating disintegration tests for CLC-C25 tablets containing Lactose 100 mesh® as a filler.
Figure 3:
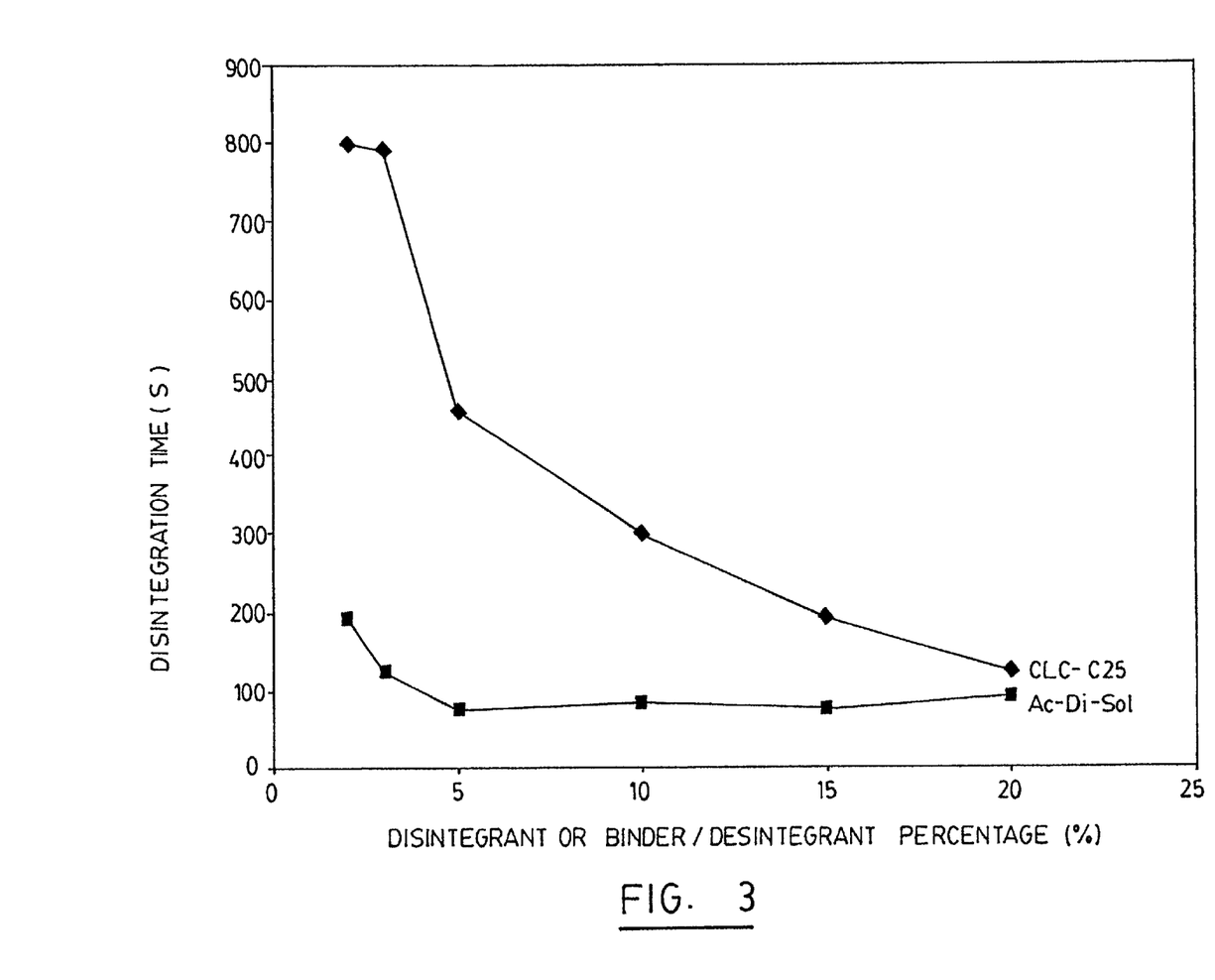
FIG. 3 is a curve illustrating disintegration tests for CLC-C25 tablets containing Spray-dried lactose® as a filler.

Avicel PH101® and Ac-Di-Sol™ as binding/disintegrants, are shown in FIGS. 1–3 and the following Table 2.

TABLE 2

Disintegration test for tablets containing a filler, various percentages of disintegrant or binder/disintegrant and 0.5% of magnesium stearate

| Filler (%) | Disintegrant (%) | Disintegration time (s) CLC-C25 | Ac-Di-Sol ™ | Avicel PH101 ® | Avicel PH102 ® |
|---|---|---|---|---|---|
| Emcompress ® add to 100 | 2 | 18.7 ± 0.7 Agg[1] | 5.0 ± 0.1 | — | — |
|  | 3 | 16.7 ± 0.7 Agg | 4.7 ± 0.3 | — | — |
|  | 5 | 15.0 ± 0.6 | 7.4 ± 0.2 | 266 ± 8 Agg. | >1200 |
|  | 10 | 5.4 ± 0.2 | 13.0 ± 0.9 | 177 ± 3 Agg. | >1200 |
|  | 15 | 5.5 ± 0.2 | 17.3 ± 1.2 | 121 ± 1 Agg. | >1200 |
|  | 20 | 5.2 ± 0.3 | 29.3 ± 0.3 | 72 ± 6 Agg. | >1200 |
| Lactose 100 mesh ® add to 100 | 2 | 15.9 ± 0.2 | 13.8 ± 0.2 | — | — |
|  | 3 | 16.9 ± 0.5 | 17.2 ± 0.8 | — | — |
|  | 5 | 16.1 ± 0.1 | 24.8 ± 0.9 | 16.0 ± 0.5 | 3.97 ± 0.3 |
|  | 10 | 13.9 ± 0.4 | 40.5 ± 1.6 | 13.7 ± 1.2 | 15.3 ± 0.7 |
|  | 15 | 14.6 ± 0.2 | 51.1 ± 1.6 | 11.3 ± 0.3 | 16.0 ± 0.5 |
|  | 20 | 14.9 ± 0.2 | 69.0 ± 2.4 | 10.0 ± 0.5 | 20.0 ± 0.9 |
| Spray dried lactose ® add to 100 | 2 | 800 ± 29 | 192 ± 6 | — | — |
|  | 3 | 790 ± 22 | 125 ± 12 | — | — |
|  | 5 | 460 ± 16 | 75 ± 8 | >1080 | >1200 |
|  | 10 | 299 ± 14 | 83 ± 6 | >1080 | >1200 |
|  | 15 | 192 ± 5 | 74 ± 4 | >1080 | >1200 |
|  | 20 | 122 ± 9 | 92 ± 3 | >1080 | >1200 |

[1] Agg. means aggregates.

EXAMPLE 1
Cross-linking of microcrystalline cellulose: CLC-C25 synthesis 20 ml of NaOH 1N was added to 15 g of microcrystalline cellulose (Avicel PH101®, FMC Corp., Avicel sales Philadelphia, U.S.A.). The system was homogenised for 10 minutes on ice (T°<5° C.). For the synthesis of CLC-C25, 3.2 ml (d=1.18 g/ml) of epichlorohydrin (Sigma Chemical Company, St. Louis, U.S.A.) was added gradually and homogenisation continued for another 15 minutes. The milky solution obtained was then heated gradually to 60–65° C. Once system temperature reached 50° C., the milky solution changed to a yellowish colour. The system was heated for one hour and a half at 60–65° C. The CLC gel was then neutralised with distilled water and washed twice through a Büchner funnel with a solution of 85/15 acetone/water and finally twice more with 100% acetone. The resulting solid gel was exposed overnight to air.

By proceeding in the same manner, different cross-linking degrees can be obtained by simply varying the epichlorohydrin/cellulose ratio. As aforesaid, this ratio is expressed in terms of g of epichlorohydrin/100 g of cellulose and is defined as the cross-linking degree (CLD).

EXAMPLE 2
CLC-C25 disintegrating properties

The results of the comparative disintegration studies made on tablets containing CLC-C25 as prepared in example 1, Avicel PH101® and Ac-Di-Sol™ as binding/disintegrants, are shown in FIGS. 1–3 and the following Table 2.

Tablets containing Emcompress® as an insoluble filler (see FIG. 1 and Table 2) clearly proved the high efficiency of CLC-C25 as a disintegrant when used in an amount of 10 to 20% by weight in the tablets, as compared to Avicel PH101®. On the other hand, tablets containing CLC-C25 were disintegrated 3–5 times faster than those containing Ac-Di-Sol™. FIG. 1 also shows that an increase in the excipients concentration increased the disintegration time except for CLC-C25, with which, when present in an amount of 10 to 20% by weight, the tablets were disintegrated at a speed of 3–5 times faster than with Ac-Di-Sol™.

Tablets containing Lactose 100 mesh® as a soluble filler also proved the high ability of CLC-C25 as a disintegrant used in an amount of 10–20% by weight, as compared to the superdisintegrant Ac-Di-Sol™ and to the binding/disintegrating agents Avicel PH101® and Avicel PH102® (FIG. 2). Lactose 100 mesh® tablets showed the same effect of the excipient concentration on the disintegration time as in Emcompress® tablets. On the other hand, Lactose 100 mesh® tablets took longer to disintegrate than Emcompress® tablets.

Tablets containing spray-dried lactose® as highly soluble filler showed a significant increase in disintegration time as compared to the results obtained for Emcompress® and Lactose 100 mesh® (FIG. 3). Although it took twice the time for CLC-C25 to disintegrate spray-dried lactose® tablets as compared to the superdisintegrant Ac-Di-sol™, CLC-C25 can still be considered an excellent disintegrant, when used in an amount of 10–20% by weight (Table 2).

One can deduce the effect of the filler solubility on the disintegration time of the tablet: the more soluble is the filler, the longer is the disintegration time of the tablet.

In conclusion, according to these data, CLC-C25 is obviously an interesting disintegrant. Its disintegrating properties are comparable to those of a superdisintegrant no matter the solubility of the filler used in the formulation, contrary to the case of the superdisintegrant Ac-Di-Sol™ and the binder/disintegrant Avicel PH101® and Avicel PH102®.

EXAMPLE 3

CLC-C25 binding properties

Figure 4:
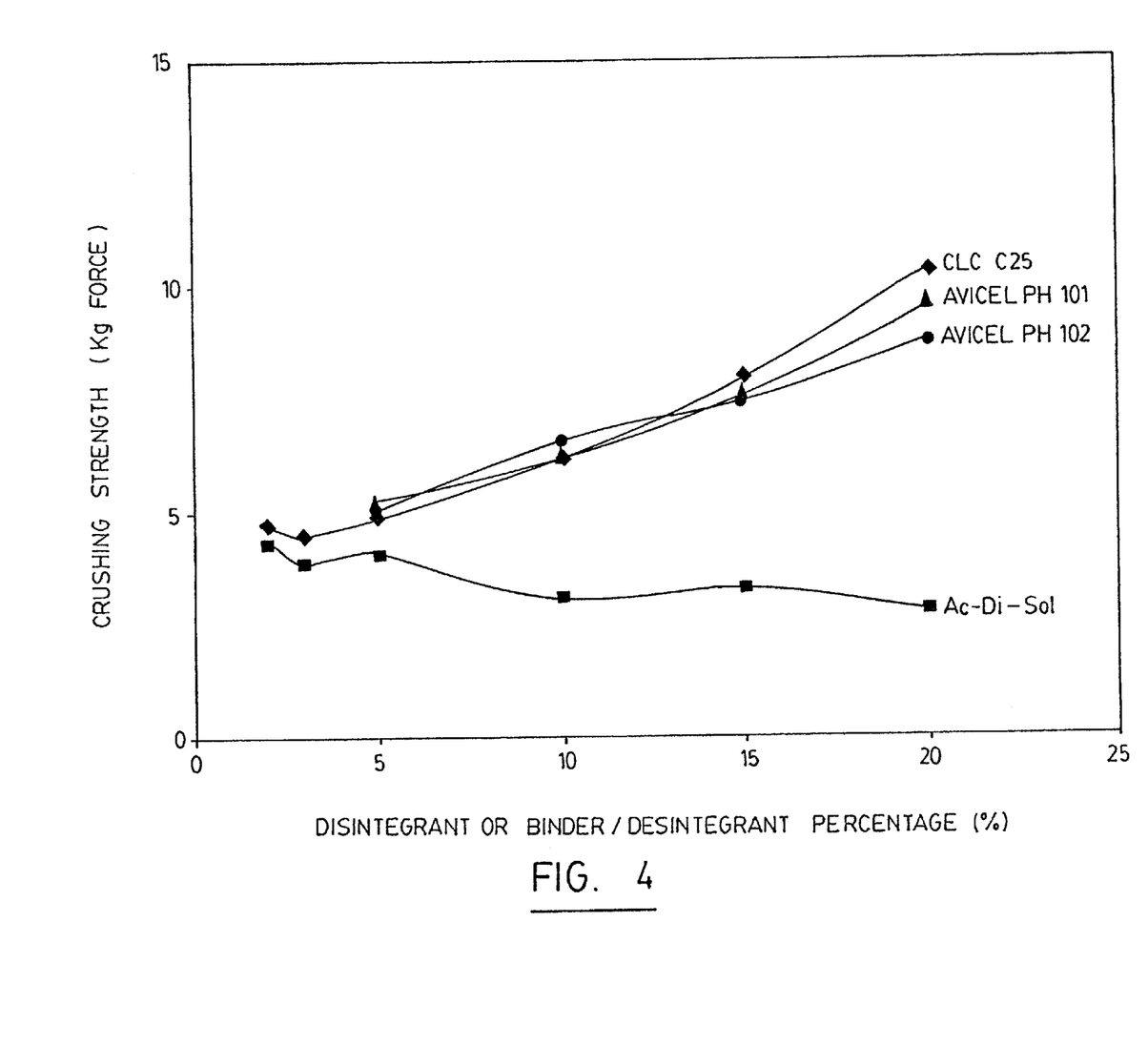
FIG. 4 is a curve illustrating hardness tests for CLC-C25 tablets containing Encompress® as a filler.
Figure 5:
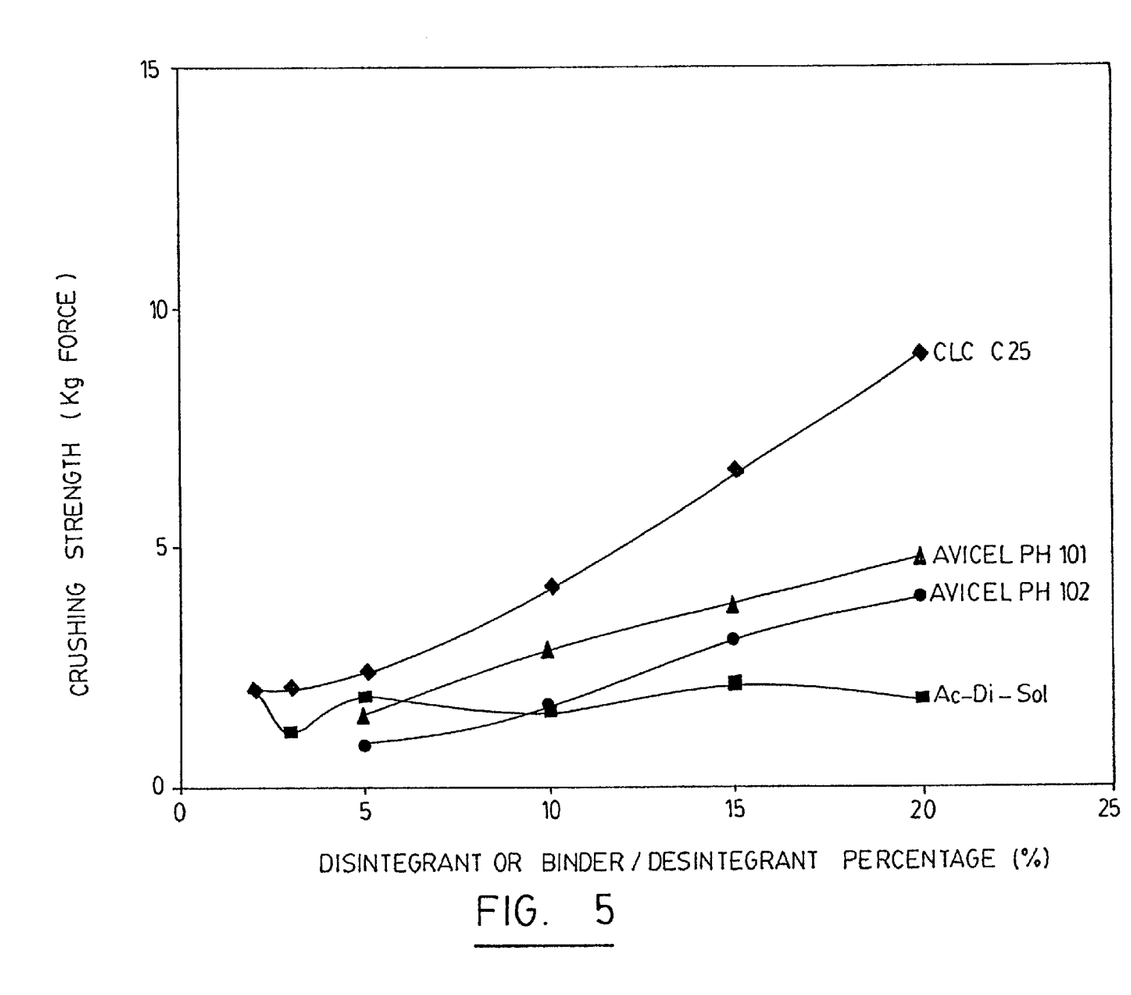
FIG. 5 is a curve illustrating hardness tests for CLC-C25 tablets containing lactose 100 mesh® as a filler.
Figure 6:
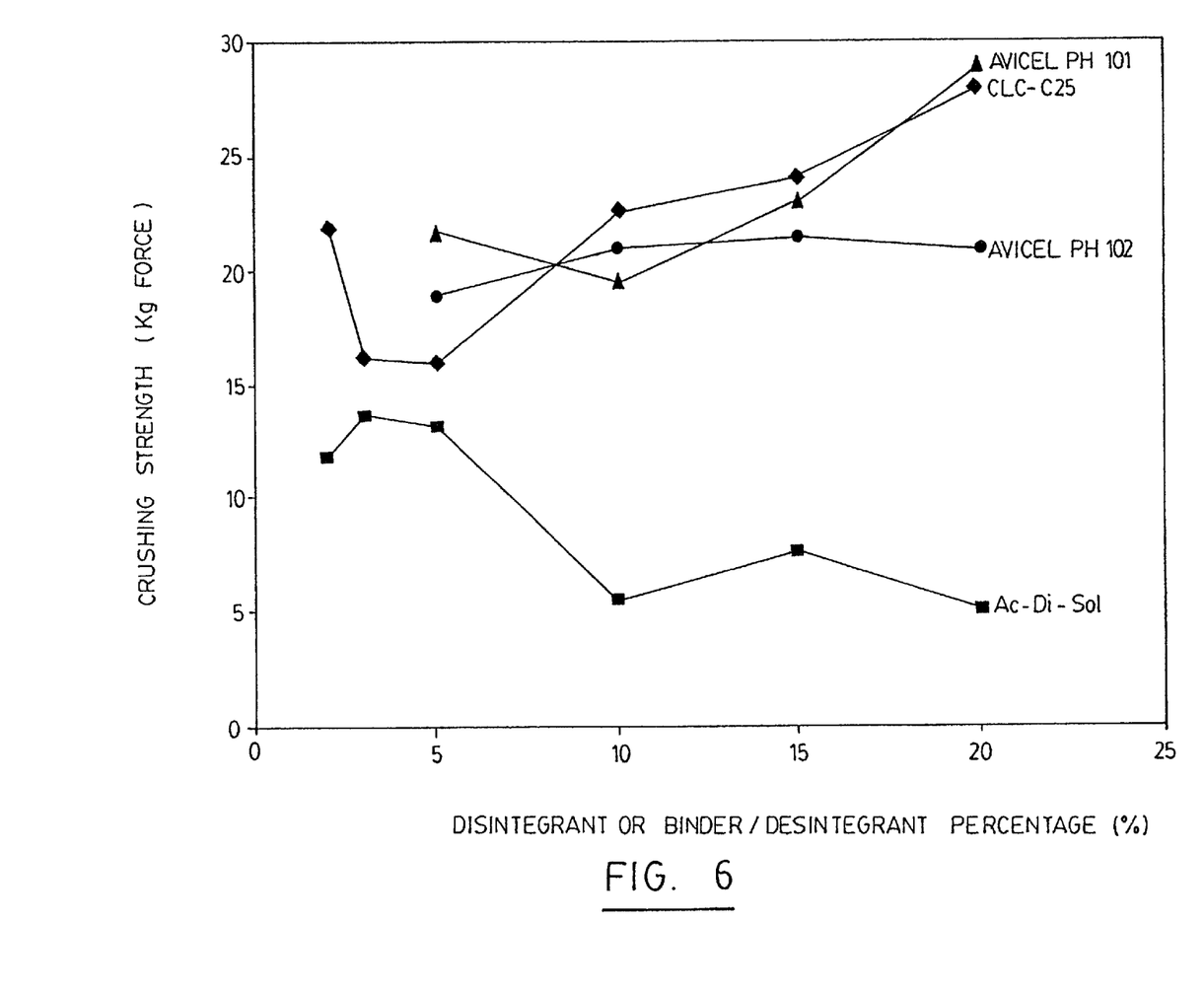
FIG. 6 is a curve illustrating hardness tests for CLC-C25 tablets containing Spray-dried lactose® as a filler.

The results shown in FIGS. 4 to 6 and the following Table 3 prove that CLC-C25 can be used as an excellent tablet binder.

TABLE 3

Hardness test for tablets containing a filler, various percentages of disintegrant or binder/disintegrant and 0.5% of magnesium stearate

| Filler | Disintegrant | Crushing strength (kg force) | | | |
|---|---|---|---|---|---|
| (%) | (%) | CLC-C25 | Ac-Di-Sil ™ | Avicel PH101 ® | Avicel PH102 ® |
| Emcompress ® | 2 | 4.7 ± 0.1 | 4.3 ± 0.1 | — | — |
| add to 100 | 3 | 4.5 ± 0.1 | 3.9 ± 0.1 | — | — |
| | 5 | 4.9 ± 0.1 | 4.1 ± 0.1 | 5.3 ± 0.1 | 5.1 ± 0.1 |
| | 10 | 6.2 ± 0.3 | 3.1 ± 0.1 | 6.3 ± 0.1 | 6.6 ± 0.4 |
| | 15 | 8.0 ± 0.4 | 3.3 ± 0.1 | 7.6 ± 0.3 | 7.5 ± 0.1 |
| | 20 | 10.3 ± 0.1 | 2.8 ± 0.1 | 9.6 ± 0.1 | 8.5 ± 0.1 |
| Lactose 100 | 2 | 2.0 ± 0.1 | 2.1 ± 0.4 | — | — |
| mesh ® | 3 | 2.1 ± 0.1 | 1.2 ± 0.2 | — | — |
| add to 100 | 5 | 2.4 ± 0.6 | 1.9 ± 0.1 | 1.6 ± 0.3 | 0.9 ± 0.1 |
| | 10 | 4.2 ± 0.1 | 1.6 ± 0.1 | 2.9 ± 0.3 | 1.7 ± 0.3 |
| | 15 | 6.6 ± 0.5 | 2.2 ± 0.1 | 3.8 ± 0.1 | 3.1 ± 0.1 |
| | 20 | 9.1 ± 0.3 | 1.9 ± 0.2 | 4.8 ± 0.1 | 4.0 ± 0.1 |
| Spray-dried | 2 | 21.9 ± 0.9 | 11.8 ± 0.2 | | |
| lactose ® | 3 | 16.3 ± 0.6 | 13.7 ± 0.6 | | |
| add to 100 | 5 | 16.1 ± 2.1 | 13.2 ± 0.2 | 21.7 ± 0.8 | 19.0 ± 0.3 |
| | 10 | 22.6 ± 0.2 | 5.6 ± 0.1 | 19.6 ± 0.8 | 21.0 ± 0.6 |
| | 15 | 24.1 ± 0.6 | 7.7 ± 0.9 | 23.1 ± 0.4 | 21.5 ± 0.6 |
| | 20 | 28.2 ± 0.7 | 5.2 ± 0.4 | 29.1 ± 0.4 | 21.0 ± 0.3 |

As can be seen, the hardness of the tablets containing Emcompress® as an insoluble filler increased when the excipient concentration increased (10–20%). CLC-C25-containing tablets were the hardest when CLC-C25 was used in an amount of 10–20% by weight in the tablets, as compared to Avicel PH101® and Avicel PH102® while the hardness of the tablets with Ac-Di-Sol™ decreased when the concentration of this product increased (FIG. 6).

Tablets containing Lactose 100 mesh® as soluble filler also showed the efficiency of CLC-C25 as a binder (FIG. 2). The CLC-C25-containing tablets were the hardest.

Tablets containing spray-dried lactose® as a highly soluble filler were also the hardest. As seen in FIG. 3, the CLC-C25-containing tablets were as hard as the Avicel PH101®-containing tablets. The hardness of the Avicel PH102®-containing tablets was somehow stable. The Ac-Di-Sol™-containing tablets presented a slight decrease in the crushing strength as its concentration increased.

According to the results of this hardness study, CLC-C25 powder seems to be a more effective binding material than Ac-Di-Sol™, thereby proving that CLC-C25 is an effective disintegrant with high binding properties. On the other hand, CLC-C25 binding properties are comparable or even superior in some instances to those of commercial microcrystalline cellulose materials, like Avicel PH101® and Avicel PH102®, thereby illustrating the ability of CLC-C25 as a binder with disintegrating properties of a superdisintegrant.

EXAMPLE 4

Water uptake

The results of the tests reported in the following Table 4, obtained show that Avicel PH101®, Avicel PH102® and CLC-C25 promoted no swelling since their swelling capacity ratio was approximately equal to 1. This proves that CLC-C25 does not disintegrate the tablets by a swelling mechanism but rather by adsorption of water molecules, filling the void space and exerting an opposite force to those keeping the macromelecular chains together.

TABLE 4

Swelling of excipients

| Excipient | Swelling capacity $V(H_2O)/V(paraffin)$ |
|---|---|
| Avicel PH101 ® | 0.95 |
| Avicel PH102 ® | 0.95 |
| CLC-C25 | 0.92 |
| Ac-Di-Sol ® | reference[1] |

[1]as mentioned in the following publication [Gissinger D. et al., A comparative study of cross-linked carboxymethylcellulose as tablet disintegrant. Pharm. Ind. 42(2), 189–192 (1980)], Ac-Di-Sol ™ tends to swell to 200 times of its volume.

EXAMPLE 5

Cross-linking of fibrous cellulose: CLC-F40 synthesis

Different cross-linked celluloses were prepared using fibrous cellulose (Sigmacell® type 101, Sigma Chemical Company, St Louis, USA) as a starting material. The cross-linking was carried out in the same manner as in Example 1.

Tablets weighing 500 mg and containing 3% of CLC-F40, 15% of Acetaminophen as a model drug, 0.5% of magnesium stearate as a lubricant and Spray-dried lactose® as a diluent, were compressed at 2 tons/cm$^2$ on a hydraulic press (C-30 Research & Industrial Instruments Company, London, U.K.).

The dissolution of acetaminophen tablets containing CLC-F40 was studied in a number two U.S.P. XX dissolution apparatus, in an acidic medium (HCl solution, pH 1.00). Tablets were placed individually in 900 ml beakers at 37° C. in a dissolution system (Distek Dissolution System 2100A, Distek Inc., North Brunswick, N.J. U.S.A.), equipped with a rotating paddle (50 rpm). The drug release was followed spectrophotometrically at 242 nm on a HP spectrophotometer (Hewlett Packard 8452A, Diode Array Spectrophotometer, California, U.S.A.). 1 mL sample per unit of time was drawn up manually. Three measurements were taken for each tablet formulation. Mean values and standard deviations were calculated.

Figure 7:
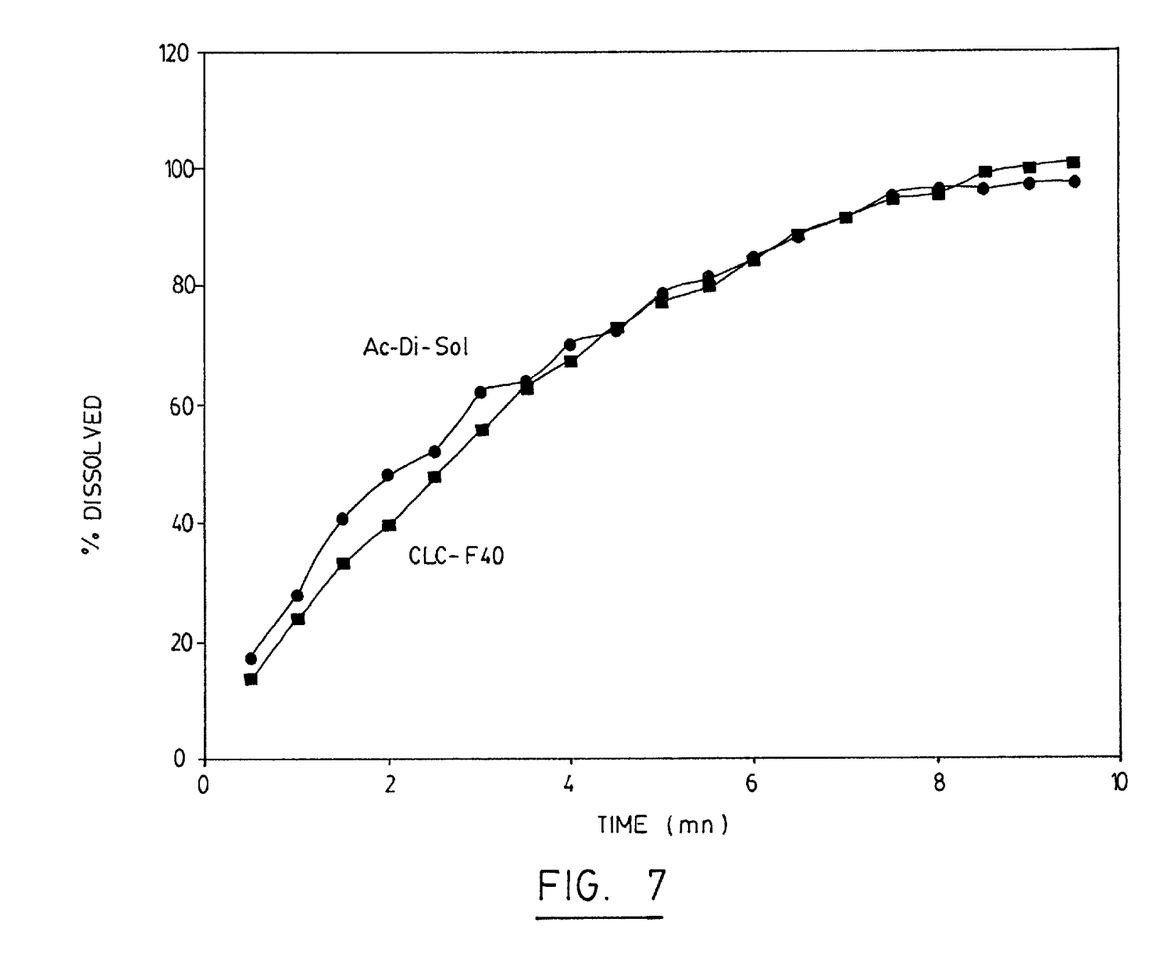
FIG. 7 is a curve illustrating dissolution tests for Acetaminophen tablets containing 10% of CLC-F40.

The obtained results are reported in FIG. 7. As can be seen, CLC-F40 has he properties of a superdisintegrant. Indeed, when added in concentrations as low as 3%, CLC-F40 provoked super fast disintegration of the compressed tablets.

We claim:

1. A pharmaceutical tablet consisting of a compressed dry mixture of a powder of at least one pharmaceutically active ingredient with a powder of at least one pharmaceutical excipient including a binder/disintegrant present in an amount equal to or lower than 35% by weight with respect to the total weight of the tablet, wherein said binder/disintegrant is a pharmaceutically acceptable, non-swelling cross-linked cellulose having a cross-linking degree ranging from 2 to 50, said cross-linked cellulose being prepared by cross-linking a cellulose selected from the group consisting of fibrous cellulose and microcrystalline cellulose, with a cross-linking agent in a relative amount of 2 to 50 g of said cross-linking agent per 100 g of said cellulose.

2. The pharmaceutical tablet of claim 1, wherein the cross-linked cellulose has a cross-linked degree ranging from 3 to 40.

3. The pharmaceutical tablet of claim 2, wherein the cross-linked cellulose has a cross-linking degree ranging from 3 to 20.

4. The pharmaceutical tablet of claim 2, wherein the cross-linked cellulose has a cross-linking degree ranging from 20 to 30.

5. The pharmaceutical tablet of claim 2, wherein the cross-linked cellulose has a cross-linking degree ranging from 30 to 40.

6. The pharmaceutical tablet of claim 2, wherein the cross-linked cellulose is present in the tablet in an amount ranging from 2 to 20% by weight with respect to the total weight of said tablet.

7. The pharmaceutical tablet of claim 6, the cross-linked cellulose is present in the tablet in an amount ranging from 10 to 20% by weight with respect to the total weight of said tablet.

8. The pharmaceutical tablet of claim 2, wherein the cellulose used to prepare the cross-linked cellulose is a fibrous cellulose.

9. The pharmaceutical tablet of claim 8, wherein the cross-linking agent is epichlorhydrin and the cross-linked cellulose has a cross-linking degree of 40.

10. The pharmaceutical tablet of claim 2, wherein the cellulose used to prepare the cross-linked cellulose is a microcrystalline cellulose.

11. The pharmaceutical tablet of claim 10, wherein the cross-linking agent is epichlorhydrin and the cross-linked cellulose has a cross-linking degree of 25.

12. The pharmaceutical tablet of claim 2, wherein the cross-linking agent is selected from the group consisting of epichlorhydrin, sodium trimetaphosphate, adipic-acetic anhydride, phosphorous oxychloride, formaldehyde and diepoxides.

13. The pharmaceutical tablet of claim 2, wherein:
the cellulose used to prepare the cross-linked cellulose is selected from the group consisting of fibrous cellulose and microcrystalline cellulose;
the cross-linking agent is selected from the group consisting of epichlorhydrin, sodium trimetaphosphate, adipic-acetic anhydride, phosphorus oxychloride, formaldehyde and diepoxides; and
the cross-linked amylose is present in the tablet in an amount ranging from 10 to 20% by weight with respect to the total weight of said tablet.

14. The pharmaceutical tablet of claim 13, wherein said at least one pharmaceutical excipient also includes at least one other additives selected from the group consisting of diluents, fillers and lubricants.

* * * * *

UNITED STATES PATENT AND TRADEMARK OFFICE
CERTIFICATE OF CORRECTION

PATENT NO. : 5,989,589                           Page 1 of 2
DATED       : November 23, 1999
INVENTOR(S) : Louis CARTILIER and Chafic CHEBLI It is certified that error appears in the above-identified patent and that said Letters Patent is hereby corrected as shown below:

Cover page, item (56), line 10: replace "Cartlilier" by --Cartilier--;

Column 2,    line 34: replace "what" by --that--;

Column 3,    line 60: replace "epichlorhydrin" by --epichlorohydrin--;

Column 5,    line 4: replace "diluent)" by --diluent(--;
             line 11: add --to-- after "superior";
             line 47: replace "form" by --from--;

Column 6,    line 63: replace "13363" by --1363--;

UNITED STATES PATENT AND TRADEMARK OFFICE
CERTIFICATE OF CORRECTION

PATENT NO. : 5,989,589
DATED : November 23, 1999
INVENTOR(S) : Louis Cartilier and Chafic Chebli It is certified that error appears in the above-identified patent and that said Letters Patent is hereby corrected as shown below:

Column 8, Table 2, last column, line 9: replace "3.97 ± 0.3" by —39.7±3—;

Column 9, Table 3, 4th column: replace "Ac-Di-Sil" by —Ac-Di-Sol—;
last column, line 6: replace "8.5 ± 0.1" by —8.8 ± 0.1—;

Column 12, line 1: Add —wherein— after "claim 6,";
lines 9, 15, 19 and 27: replace "epichlorhydrin" by
—epichlorohydrin—; and
line 30: replace "amylose" by —cellulose—.

Signed and Sealed this

Fifth Day of September, 2000

*Attest:*

Q. TODD DICKINSON

*Attesting Officer*  *Director of Patents and Trademarks*